United States Patent [19]

Rudigier et al.

[11] Patent Number: 5,738,825
[45] Date of Patent: Apr. 14, 1998

[54] OPTICAL BIOSENSOR MATRIX

[75] Inventors: Helmut Rudigier, Bad Ragaz, Switzerland; Roland Pfefferkorn, Feldkirch-Tisis, Austria; Kurt Tiefenthaler, Zurich, Switzerland; Véronique Briquet, Chalet Casse, Switzerland; Alois Zetting, Herrliberg, Switzerland; Peter Marbach, Therwil, Switzerland; Francois Legay, Huninque, France; Peter End, Basel, Switzerland

[73] Assignees: Balzers Aktiengesellschaft, Furstentum, Liechtenstein; Artificial Sensing Instruments ASI AG, Zurich, Switzerland

[21] Appl. No.: 854,586
[22] PCT Filed: Jul. 18, 1994
[86] PCT No.: PCT/EP94/02361
 § 371 Date: Apr. 27, 1995
 § 102(e) Date: Apr. 27, 1995
[87] PCT Pub. No.: WO95/03538
 PCT Pub. Date: Feb. 2, 1995

Related U.S. Application Data

[63] Continuation of Ser. No. 397,281, Apr. 27, 1995, abandoned.

[30] Foreign Application Priority Data

Jul. 20, 1993 [GB] United Kingdom ............ 9314991

[51] Int. Cl.⁶ .................................................. G01N 21/01
[52] U.S. Cl. ........................................ 422/82.11; 422/102
[58] Field of Search ...................... 422/82.11, 102; 436/42, 164, 165

[56] References Cited

U.S. PATENT DOCUMENTS 5,082,629  1/1992  Burgess et al. ............ 422/82.11

OTHER PUBLICATIONS

Advertising Brochure of Packard/TopCount, no date supplied.

Primary Examiner—Lyle A. Alexander
Attorney, Agent, or Firm—Notaro & Michalos P.C.

[57] ABSTRACT

A detection cell which is used as a component of an optical biosensor comprises a transparent base plate and a sample plate on the base plate. The sample plate has a matrix of wells extending through it to each to receive a sample. The base plate includes a waveguiding film and a diffraction grating means to in couple an incident light field into the waveguiding film beneath a well to generate a diffracted light field to enable detection of a change in the effective refractive index of the waveguiding film.

12 Claims, 7 Drawing Sheets

OPTICAL BIOSENSOR MATRIX

This application is a continuation of application Ser. No. 08/397,281, filed Apr. 27, 1995 now abandoned.

FIELD AND BACKGROUND OF THE INVENTION

This invention relates to the field of optical biosensors and the application of optical biosensors to biochemical analysis, particularly in combination with standard biochemical analysis techniques and equipment to permit automated analysis.

Optical biosensors are devices which make use of the refractive and coupling properties of light to detect the presence of substances on a surface. Usually integrated optical biosensors have a waveguiding film, of a certain refractive index, which forms the surface which the sample of the substance contacts. A base sheet, which has a lower refractive index than the waveguiding film, contacts the waveguiding film. A grating coupler or prism coupler is then positioned to cooperate with the base sheet to incouple light that is shone on the base sheet through the coupler. Monochromatic light is then shone on the base sheet through the coupler and the in- or out-coupled light monitored. Changes in the refractive index of the waveguiding film caused by molecules binding to it can be detected by observing changes in the angle of the emitted, out-coupled light. To detect the presence of specific substances in the sample, the waveguiding film can be coated with a complementary substance which specifically binds to the first substance.

An example of a biosensor that uses a grating coupler is disclosed in European Patent 0 226 604 B. This biosensor comprises a base sheet joined to a waveguiding film; the surfaces of the sheet and film that join together being formed into a grating coupler or Bragg coupler. This grating coupler can be a unidiffractive or multidiffractive structure. The refractive index of the waveguiding film is higher than that of the base sheet. A chemo-sensitive substance is coated on the waveguiding film in an area of the waveguiding film that contacts the sample. A laser is used to direct monochromatic light towards the grating coupler at a selected angle of incidence. The position of the laser or of the grating coupler is then altered to change the angle of incidence until light is incoupled in the waveguiding film. Any change in the effective refractive index caused by molecules binding to the waveguiding film, disturbs the incoupling condition and the angle of incidence must be changed to correct for this. Hence changes in the angle of incidence (and this correlates directly to the position of the laser with respect to the grating coupler) required to maintain the incoupled light are monitored. These changes in the angle of incidence are then correlated to changes in the amount of molecules binding to the surface of the chemo-sensitive substance.

It will be appreciated that this biosensor provides an extremely convenient means for detecting the presence and the amount of a substance in a sample. However a drawback of the system is that the laser or grating coupler must be continually moved.

A further optical biosensor is disclosed in WO 93/01487 and this optical biosensor permits the encoupled light to be monitored without the use of moving parts. This biosensor relies on the use of a fan-shaped, monochromatic light field which may be coupled in and out of the waveguiding structure. The outcoupled light field can be focussed to a point and the position of the point determined. Movement in the position of the point indicates changes in the effective refractive index of the waveguiding structure.

Optical biosensors provide a very convenient means of detecting the presence of substances without the use expensive reagents and labelling techniques. However at the present time, optical biosensors can only be used to test single samples which must be placed in special detection cells. Hence the laboratory technician must transport a sample to the optical biosenor, load it into the biosensor, and monitor it. Afterwards the biosensor must be cleaned. This severely limits the application of optical biosensors.

SUMMARY OF THE INVENTION

Accordingly in one aspect this invention provides a detection cell for use as a component of an optical biosenor; the detection cell comprising a transparent base plate and a sample plate on the base plate; the sample plate having a matrix of wells extending through it to each receive a sample, and the base plate including a waveguiding film and a diffraction grating means to incouple an incident light field into the waveguiding film beneath a well to generate a diffracted light field to enable the detection of a change in the effective refractive index of the waveguiding film.

Preferably the detection cell is of the same size and contains the same number of wells as a microtitre plate. Usually microtitre plates contain 6, 24 or 96 wells but the number of wells can vary as desired. Therefore the detection cell provides the significant advantage that it can be used in conjunction with standard fluid-handling systems existent in analytical laboratories. The fluid handling systems can be used to clean the detection cell, and pipette samples into the detection cell, and move the detection cell from one position to the other. The optical biosensor, of which the detection cell is a component, can then be used to analyse the contents of each well. Plainly the detection cell need not have a standard number of wells, any number of wells can be used.

The base plate may be formed of a base sheet that is covered by the waveguiding film that has a higher refractive index than the base sheet. The diffraction grating means may be formed in the base sheet, between the base sheet and the waveguiding film, or in the waveguiding film. Preferably the diffraction grating means is formed in the interface between the waveguiding film and the base sheet.

The base plate may be releasibly fixed to the sample plate so that it can be detached from the sample plate and replaced.

A separate diffraction grating means may be provided beneath each well or a single diffraction grating means, that extends over substantially the entire base plate, may be provided.

Preferably the waveguiding film is made of metal-oxide based materials such as $Ta_2O_5$, $TiO_2$, $TiO_2$—$SiO_2$, $HfO_2$, $ZrO_2$, $Al_2O_3$, $Si_3N_4$, HfON, SiON, scandium oxide or mixtures thereof. Also suitable silicon nitrides or oxynitrides (for example $HfO_xN_y$) may be used. However, especially suited materials are $Ta_2O_5$, $HfO_2$, $Si_3N_4$, $ZrO_2$, $Al_2O_3$ medium oxide, or a mixture of $SiO_2$ and $TiO_2$ or one of the oxinitrides HfON or SiON, especially $TiO_2$. Preferably the waveguiding film has a refractive index in the range 1.6 to 2.5. Also the thickness of the waveguiding film may be varied over the range 20 to 1000 nm, preferably 30 to 500 nm. The grating coupler preferably has a line density of 1000 to 3000 lines per mm, for example 1200 to 2400 lines per mm.

The base sheet is preferably made of glass or plastics (polycarbonates) and preferably has a refractive index in the range 1.3 to 1.7, for example 1.4 to 1.6.

Preferably the free surface of the waveguiding film is coated with a coupling layer that permits selective coupling of a specific substance in a well to the coupling layer. In this way, inaccuracies may be reduced. The coupling layer may be such that a reaction between it and the specific substance occurs resulting in a covalent bond or may rely on some other form of selective coupling such as antibody/antigen binding. Plainly the waveguiding film need not have a coupling layer if physical absorption, for example, of the specific substance to it provides sufficient selectivity.

In another aspect this invention provides an analytical system comprising a detection cell as defined above and a reading unit that comprises (i) at least one light source to generate and direct at least one incident light field onto the diffraction grating means beneath a well of the detection cell to provide mode excitation in the waveguiding film; (ii) at least one focusing means to focus the light field diffracted out of the waveguiding film beneath the well; and (iii) at least one position sensitive detector to monitor the position of the focussed light field.

Preferably the incident light field is generated by a laser. Also preferably more than one incident light field is provided; a light field being provided for each column of the matrix of the detection cell. If more than one light field is provided, they may be generated by providing (i) more than one light source, (ii) by splitting the field of a single light source, or (iii) by expanding a light field. Similarly more than one light detector may be provided; one light detector for each light field.

The analytical system may also comprise a transport means to transport the detection cell, from a filling station in which the wells of the detection cell are filled, to a position to enable cooperation with the reading unit.

The transport means may include position locking means so that the detection cell may be locked-into exactly the same position with respect to the reading unit on each occasion that it is desired. However the outcoupled light field alternatively may be scanned whilst the detection cell is moving with respect to the reading unit.

In a further aspect this invention provides a method for the automated analysis of samples using an optical biosensor, the method comprising filling the wells of a detection cell as defined above with a carrier fluid; transporting the detection cell to a position to cooperate with a reading unit as defined above; monitoring the out-coupled light from each well and recording it to provide a reference; transporting the detection cell to a pipetting station and pipetting a sample into each well; transporting the detection cell back to the reading unit and directing light onto the diffraction grating means in the detection cell; monitoring the out-coupled light from each well; and comparing the results obtained to the reference.

In a yet further aspect this invention provides a method for measuring the kinetics of a change in a sample, the method comprising filling the wells of a detection cell as defined above with a sample; transporting the detection cell to a position to enable cooperation with the reading unit as defined above; and monitoring repeatedly at discrete intervals the different diffracted light fields from each well; the time of each discrete interval for any cell being less than the time required for the change.

BRIEF DESCRIPTION OF THE DRAWINGS

Embodiments of the invention are now described, by way of example only, with reference to the drawings in which.

DESCRIPTION OF THE PREFERRED EMBODIMENT

Figure 1:
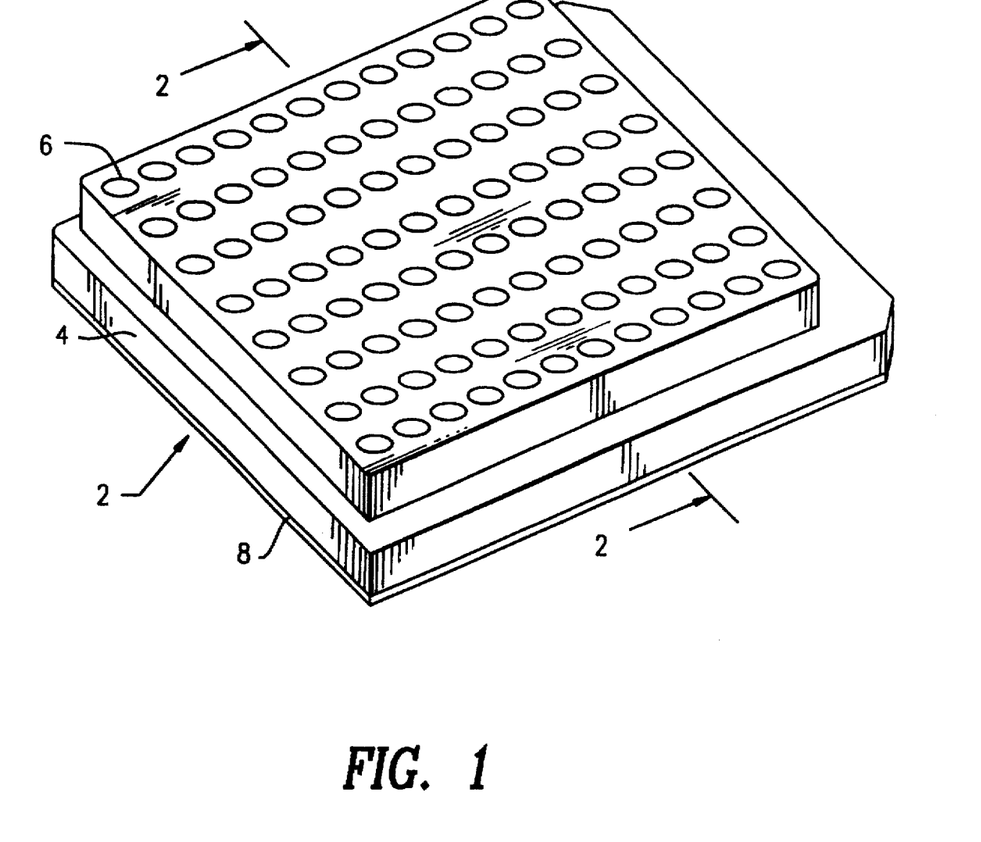
FIG. 1 is a perspective view of a detection plate.
Figure 2:
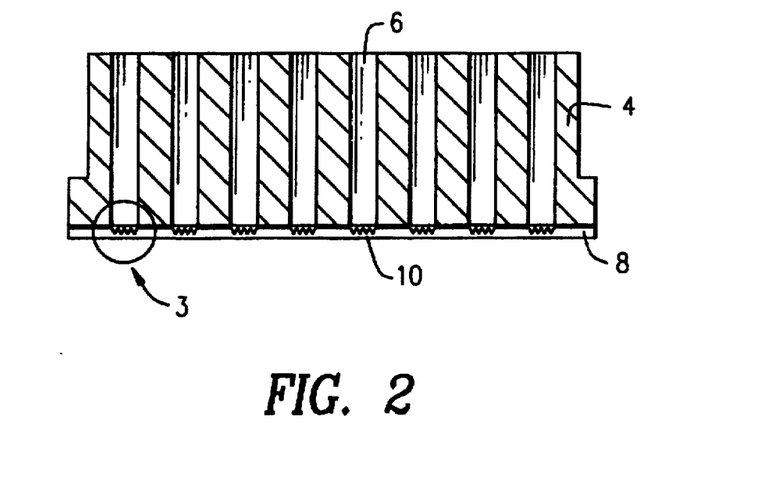
FIG. 2 is a cross-section on 2—2 of FIG. 1.

Referring to FIGS. 1 and 2, the detection cell 2 is similar in shape and appearance to a standard microtitre plate (in this case, a 96 well plate). The detection cell 2 is formed of a sample plate 4 which is rectangular in plan and which has ninety-six wells 6 extending through it; from its upper surface to its lower surface. The wells 6 are arranged in a matrix of eight columns and twelve rows, each row being spaced an equal distance from its neighbors and each column being spaced an equal distance from its neighbours. A base sheet 8 is affixed to the lower surface of the sample plate 4 and seals off the bottom of the wells 6. The base sheet 8 is preferably releasibly attached to the sample plate 4 so that it can be removed from the sample plate 4. This enables the base sheet 8 to be better washed or treated, or to be replaced when necessary.

The base plate consisting of base sheet 8 and waveguiding film 12 can also be irreversibly attached to the sample plate 4. This is attained for instance when the base plate and the sample plate 4 are ultrasonically welded together. Ultrasonic welding is possible although the waveguiding film 12 is not made up of a plastic material.

Figure 3:
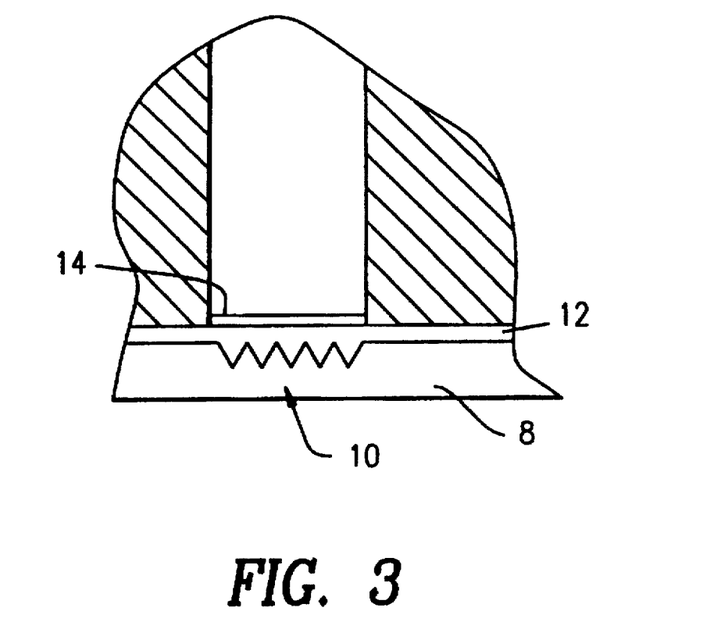
FIG. 3 is an expanded view of area 3 of FIG. 2.

The base sheet 8 is made of a suitable transparent material such as glass or plastics (for example, polycarbonates), and contains a diffraction grating 10 beneath each well 6. As is best illustrated in FIG. 3, the diffraction grating 10 is formed by a serrated interface between-the base sheet 8 and a waveguiding film 12. The waveguiding film 12 has a refractive index of about 2.43 (which is higher than that of the base sheet 8) and is made of $TiO_2$. Other suitable materials such as $Ta_2O_5$, $TiO_2$, $TiO_2$—$SiO_2$, $HfO_2$, $ZrO_2$, $Al_2O_3$, $Si_3N_4$ niobium oxide, scandium oxide, oxynitrides (for example $HfO_xN_y$), or mixtures thereof may be used. The thickness of the waveguiding film 12 is in the region of 20 to 500 nm. The density of the gratings of the diffraction grating 10 is conveniently about 1000 to 3000 lines per mm.

The diffraction grating 10 may be manufactured by lithography, embossing techniques or injection moulding.

The bottom of each well 6 may be covered with a coupling layer 14 to which only specific substances will selectively bind. For example, the coupling layer 14 can be made of an antibody which has been raised against a specific antigen. Therefore, if this antigen is present in the sample in the well 6, it will bind to the antibody in the coupling layer. However other antigens and substances in the sample should not bind to the coupling layer 14. This coupling layer 14 may be precoated on the waveguiding film 12 or may be coated on by a technician before use. Also the coupling layer 14 may be permanent or removable.

Figure 4:
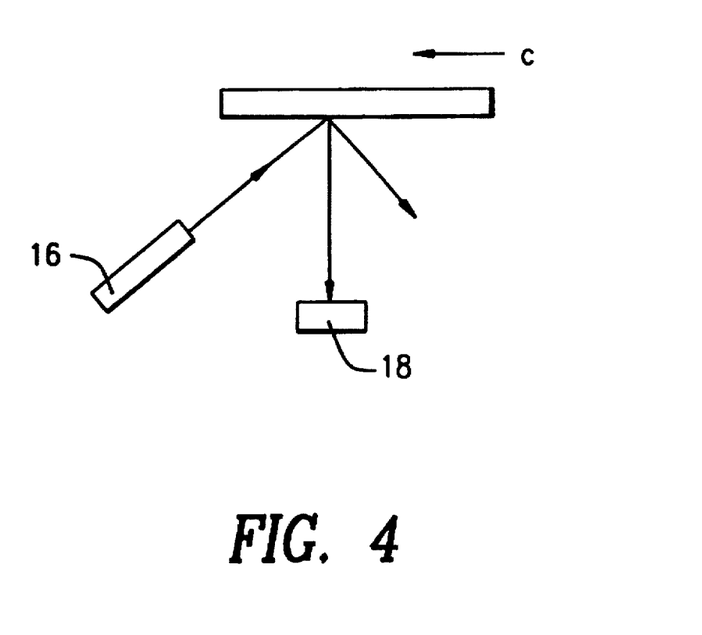
FIG. 4 is a schematic illustration of a biosensor system including a detection cell and a reading unit.

Referring to FIG. 4, an example of a detection cell 2 in use is now described. First, a detection cell 2 with or without a selected coupling layer 14 is chosen. The detection cell 2 is filled with a carrier fluid using fluid-handling equipment conventionally used with microtitre plates and is moved for example in the direction of Arrow C over a laser 16. A suitable laser is a He-Ne laser (632.8 nm) or a laser diode. As the detection cell 2 moves, the beam of light from the laser 16 strikes the diffraction grating 10 of the first well 6 in a column. This beam of light is incoupled in the waveguiding film 12 and the out-coupled beam is directed at a detector 18 where its position is detected and recorded. A suitable detector is a CCD array or a position sensitive detector. The laser and detector system disclosed in WO 93/01487 may be used. Fourier lenses are suitably used to focus the outcoupled to a point on the detector 18.

The procedure of moving the detection plate 2, scanning the diffraction grating 10 and detecting and recording the position of the out-coupled light is carried out for each well 6 in the column. To scan all the columns, a reading unit (comprising a light field and a detector) may be provided for each column. Alternatively, a reading unit may be moved along the row in the matrix before the detector plate 2 is moved to present the next row in the matrix. A suitable micro-processor (not shown) may be used to analyse and store the results. It is also possible to move the reading unit instead of the detector plate 2.

Once all wells 6 have been scanned, the detector plate 2 is moved back and samples are pipetted into the wells 6 using fluid-handling equipment conventionally used with microtitre plates. The detector cell 2 is then moved back to the reading unit to scan all wells 6 as described above. The reading obtained for each well 6 after addition of the sample is then compared to that obtained before the addition of the sample. If substances in the samples have bound to the coupling layer 14 or the free surface of the waveguiding film 12, the reading obtained would change and this would indicate the presence of the substance.

In some applications, the sample in certain wells may be replaced with carrier fluid before the detection cell 2 is moved back to the reading unit. This would ensure that the measured changes in the readings, with respect to the reference readings, caused by changes in the refractive index of the coupling layer 14, are detected.

The optical biosensor may also be used to provide information concerning the kinetics of a change in a sample; for example reaction kinetics. In this case the coupling layer 14 is selected such that a specific reaction product binds to it. Then the reactants are introduced into the well and the build up of reaction product monitored. Conveniently, this may be done in more than one well simultaneously; each well being monitored for a discrete time and then the next well being monitored and so on before returning to monitor the first well again. However the time taken to cycle back to any well must be less (preferably much less) than the time taken for the reaction to reach completion. It is also possible to use multiple incident-light fields to monitor several wells simultaneously. This will remove the need to cycle between wells.

Since an optical biosensor detects small changes in angles, it is necessary (if no other steps are taken) for the detector cell 2, after the wells have been filled with a sample, to be returned to exactly the same spacial and angular position with respect to the reading unit as previously. If this is not done, the measurements taken cannot be compared with the reference measurements.

Figure 5A:
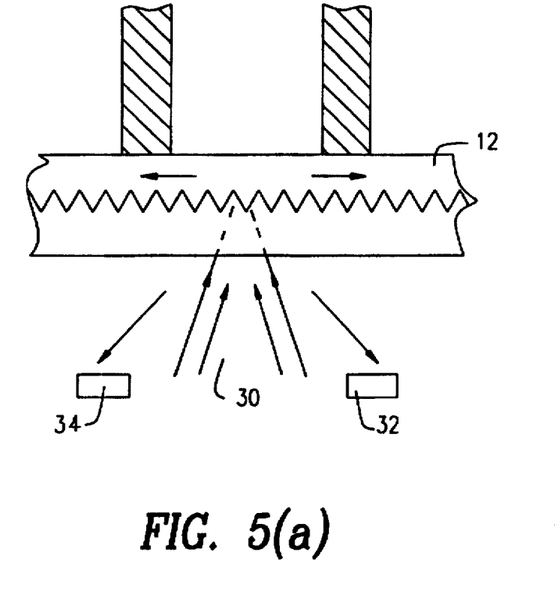
FIGS. 5(a) to 5(h) illustrate schematically several configurations for the diffraction grating means beneath a well.
Figure 5B:
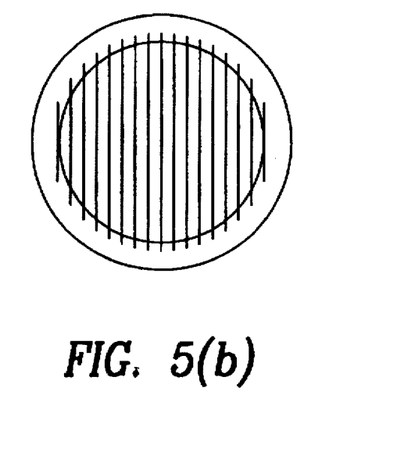

The need for precise positioning of the light beam with respect to the diffraction grating may be avoided (i) by the use of an extended grating structure which may be unidiffractional or multidiffractional (this is illustrated in FIGS. 5(a) and 5(b)) or (ii) discrete diffraction grating structures which are moved continuously with respect to the incident light beam (or vice versa). Mode excitation occurs when the incident light field impinges on an incoupling grating. Position sensitive detectors 18 then measure the positions of the outcoupled light beams; preferably at the positions of maximum incoupling. In this way, the need to return the detector cells 2 to exactly the same position with respect to the light beam can be avoided.

Figure 6A:
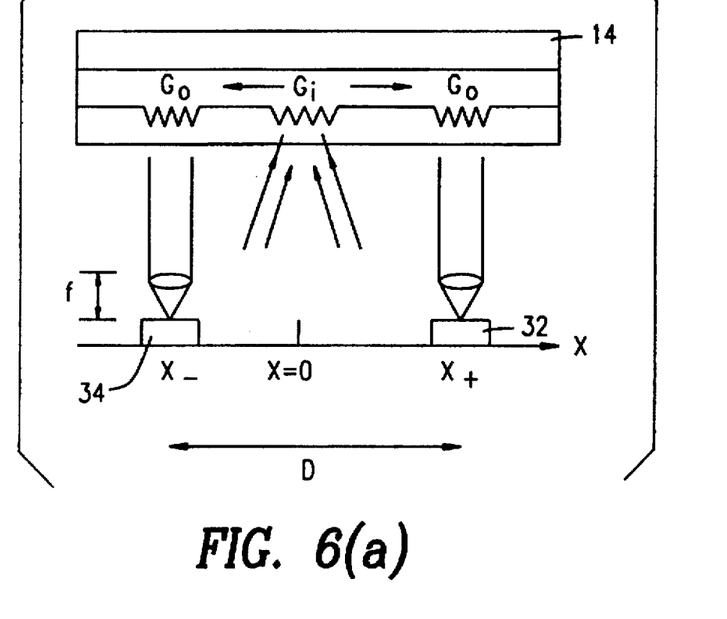
FIGS. 6(a) and 6(b) illustrate, schematically, configurations in which the absolute outcoupling angle may be determined.
Figure 6B:
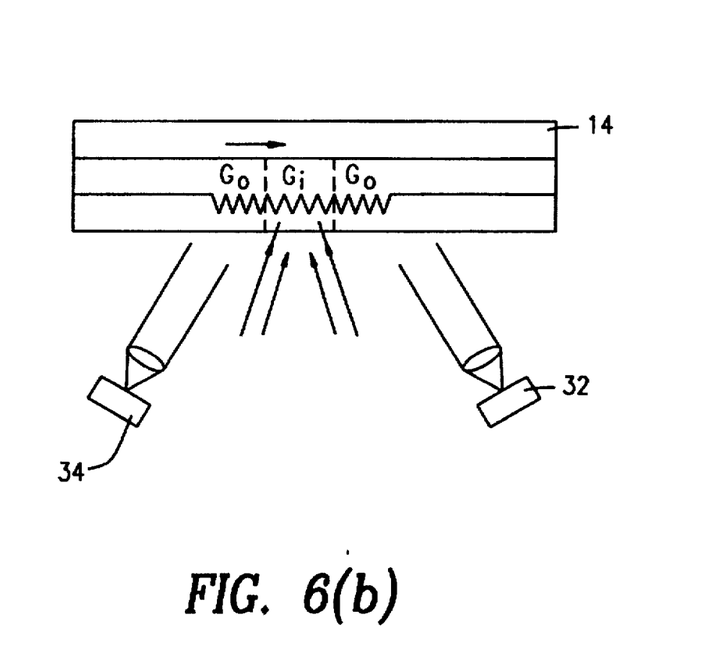

To prevent small inaccuracies in the angular position of the detection cell, the reading unit is preferably such that each well is illuminated with two incident light fields that induce mode excitation in counterpropagating directions. Also each of the two outcoupled light fields is monitored with a separate position sensitive light detector that measures the angular position of the outcoupled light field. The absolute outcoupling angle may then be determined by comparing the two readings obtained from the position sensitive detectors. A suitable method of calculating the absolute outcoupling angle is described below with reference to FIG. 6.

Figure 5C:
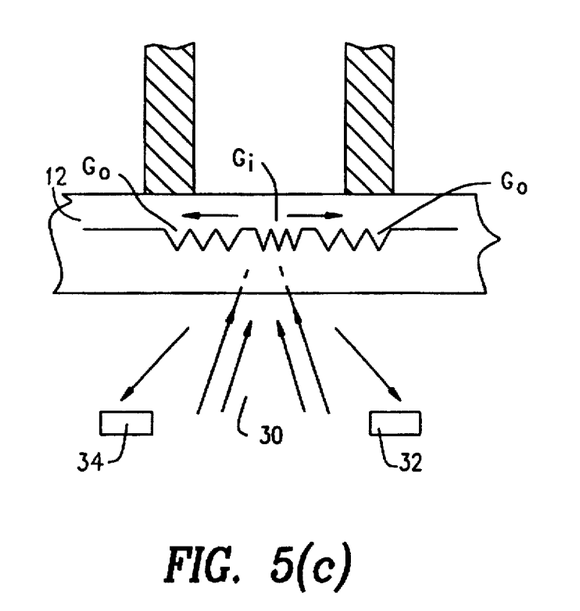

The line densities of the incoupling grating may be chosen so that mode excitation in forward and rearward directions can be brought about by one incident light field of fan shape. One part of the light beam causes mode excitation in the forward direction and the other part causes mode excitation in the rearward direction. (this is illustrated in FIGS. 5(a) and (c)).

In FIGS. 5(a) and (b), a fan shaped, incident light beam (30) is incoupled in forward and rearward directions in a waveguiding film 12 having a continuous grating. Outcoupled light in the forward direction is detected by a forward detector 32 and outcoupled light in the rearward direction is detected by a rear detector 34. The detector cell 2 need not have separate diffraction gratings 10 beneath each well 6; instead a single diffraction grating means that extends across most of the lower face of the sample plate 4 may be used. The line density of the grating plainly can be varied as desired and need not be the density given above. Also the discrete diffraction grating structures may themselves be composed of discrete gratings of preferably different line densities (this is illustrated in FIGS. 5(c) to (h).

Figure 5D:
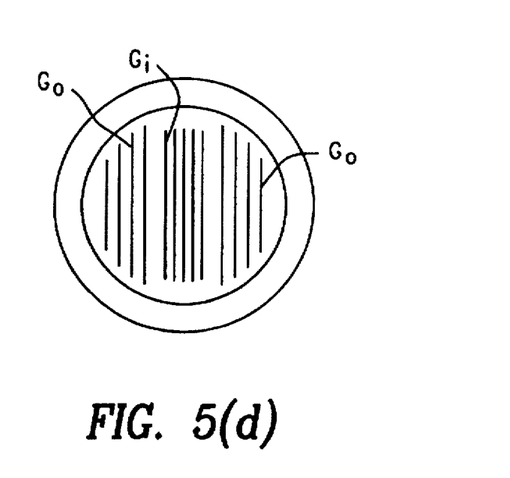

In FIGS. 5(c) and (d), a fan shaped, incident light beam (30) is incoupled in forward and rearward directions in a waveguiding film 12 having an incoupling grating $G_i$ positioned between two outcoupling gratings $G_o$. Outcoupled light in the forward direction is detected by a forward detector 32 and outcoupled light in the rearward direction is detected by a rear detector 34. The two outcoupling gratings $G_o$ may be replaced by a single large grating. In this case, two gratings would be present in the incoupling region. By choosing a high line density for the incoupling grating $G_i$, free diffracted light, which would be disturbing, may be minimized. The structure and placement of the gratings and bores thus also form optical isolating means for the matrix bores to avoid cross-talk between bores.

Figures 5E, 5F:
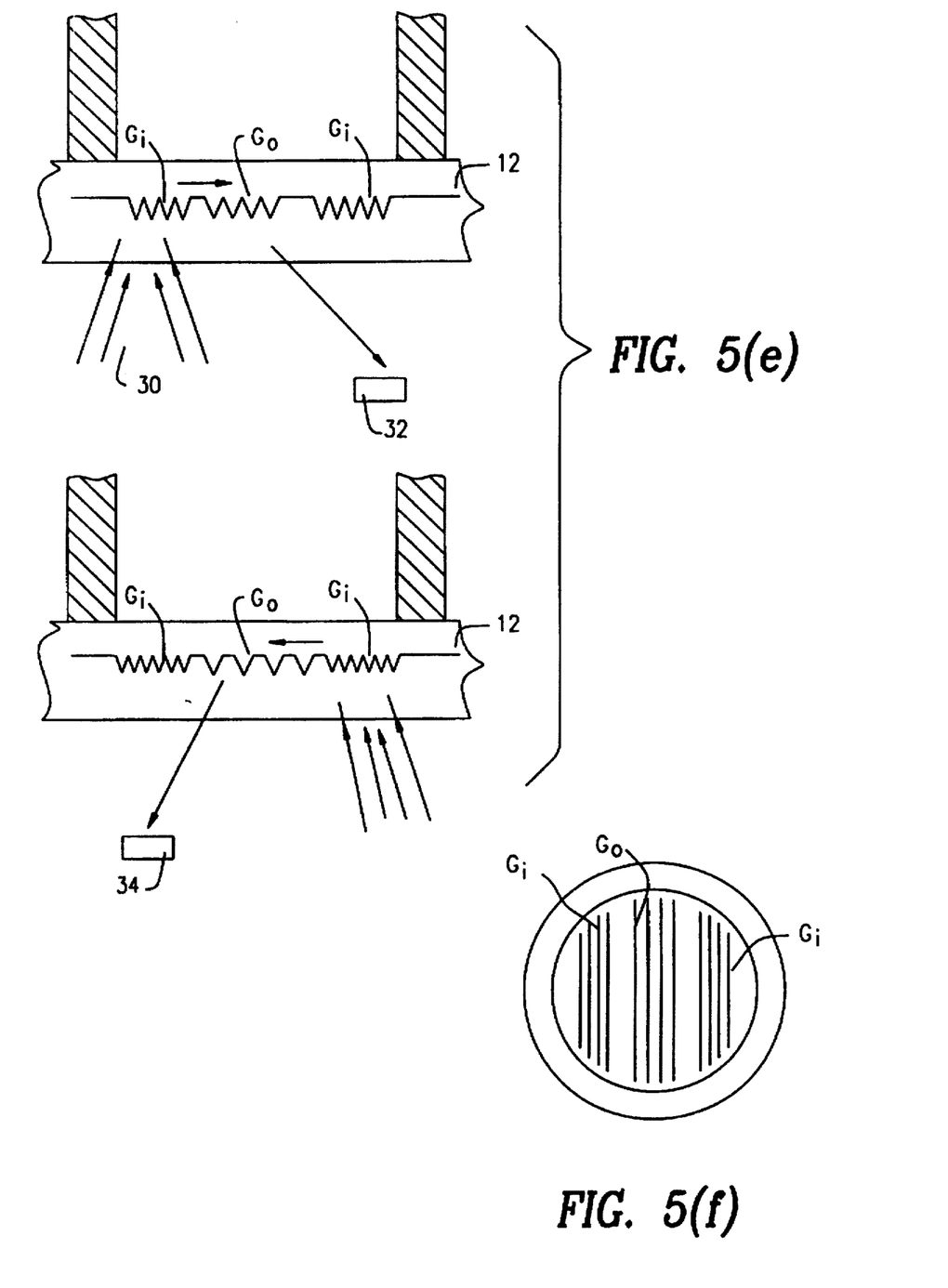

In FIGS. 5(e) and (f), a fan shaped, incident light beam (30) is incoupled in forward and rearward directions in a waveguiding film 12 having two incoupling gratings $G_i$ positioned about an outcoupling grating $G_o$. Outcoupled light in the forward direction is detected by a forward detector 32 and outcoupled light in the rearward direction is detected by a rear detector 34. For simplicity, the forward and rearward situations are shown separately, but the two incoupling gratings $G_i$ are preferably illuminated simultaneously by two, different fan shaped light beams. The incoupling and outcoupling gratings may have the same line density and may form one large discrete diffraction grating.

Figure 5G:
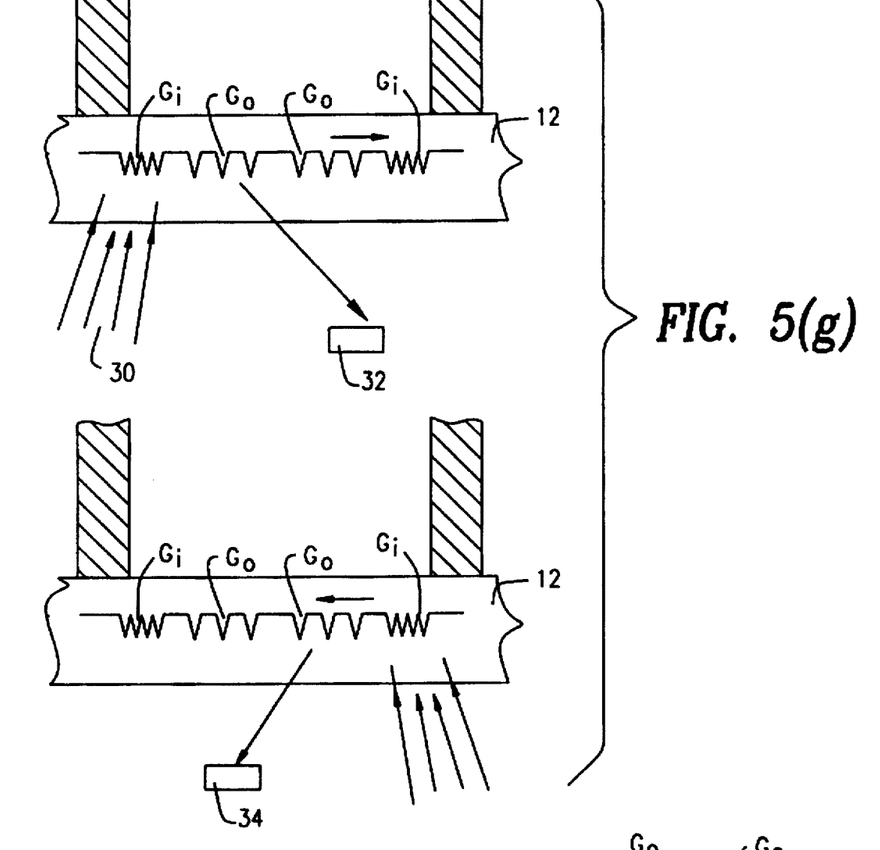
Figure 5H:
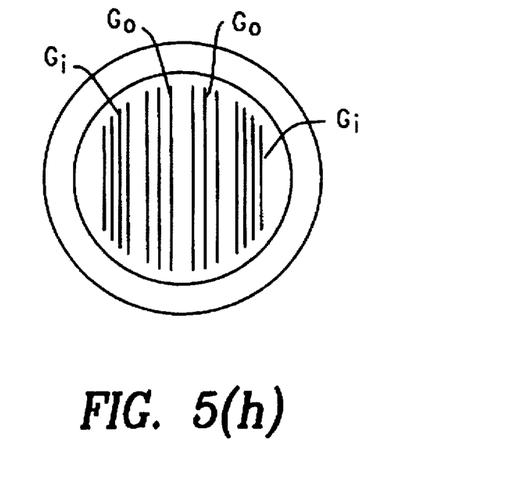

In FIGS. 5(g) and (h), a fan shaped, incident light beam (30) is incoupled in forward and rearward directions in a waveguiding film 12 having two incoupling gratings $G_i$ positioned about two outcoupling gratings $G_o$. Outcoupled light in the forward direction is detected by a forward detector 32 and outcoupled light in the rearward direction is detected by a rear detector 34. For simplicity, the forward and rearward situations are shown separately. For all off-line incubation applications (with or without using microtitre plates) the determination of an absolute sensor signal (for example an absolute outcoupling angle) is necessary. Outcoupling of a forward and rearward propagating mode using one grating is described in SPIE, Vol 1141, 192 to 200. Outcoupling of a forward and rearward propagating mode using one grating is also described in WO 93/01487.

A further possibility for determining absolute outcoupling angles consists in using two discrete outcoupling gratings or at least two different regions of a single extended outcoupling grating.

An example is illustrated in FIG. 6 where two different outcoupling gratings $G_o$ (or two different parts of one outcoupling grating) are used for outcoupling of the forward and rearward propagating mode. Incoupling occurs by diffraction of an incident, fan-shaped light field and this permits simultaneous excitation of two guided modes propagating in forward and rearward directions. The two outcoupling gratings $G_o$ operate as sensor gratings and are coated with a coupling layer 14. As may be seen from FIG. 6(a), the same grating regions would be illustrated by the forward propagating mode (or the rearward propagating mode respectively) during the reference measurement and the measurement after incubation.

The outcoupling angles are calculated from the positions $X_-$, $X_+$ of the focussed light spots on the two position sensitive detectors 32, 34 (see FIG. 6(a)). Small lateral displacements of the position sensitive detectors 32, 34 in the x-direction with respect to the reading unit do not result in a change in the positions $X_-$, $X_+$ since Fourier lenses are used. However tilting of the position sensitive detectors with respect to the x-axis causes changes in the positions $X_-$, $X_+$. In the configuration illustrated in FIG. 6(a), the absolute outcoupling angle may be calculated by first determining the absolute position $X_{abs}$ which is defined as $$X_{abs} = |X_- - (X_+ - X)/2|$$

where $X_+$ and $X_-$ are measured with respect to x=0 which is the mean position of the two position sensitive detectors. The absolute outcoupling angle $\alpha_{abs}$ is then obtained from $$\alpha_{abs} = (X_{abs} - D)/f$$

where D is the distance between the optical axes of the two Fourier lenses and f is their focal distance.

In FIG. 6(b) an arrangement is illustrated in which the beams are more separated angularly. Therefore a closer arrangement of the gratings is possible.

The diffraction grating structure may contain gratings in two directions; preferably normal directions. The gratings in one direction need not be of the same line density as those in the opposite direction. Possible configurations are illustrated in FIGS. 7(a) to (g).

Figure 7A:
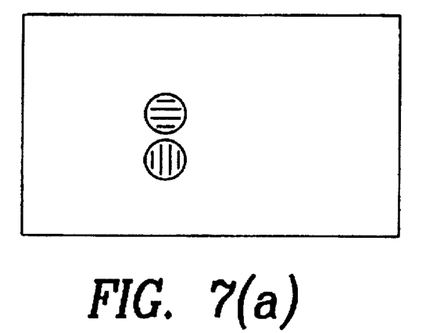
FIGS. 7(a) to 7(g) illustrate schematically several configurations for the diffraction grating means.
Figure 7B:
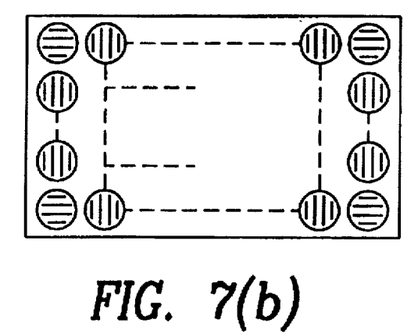
Figure 7C:
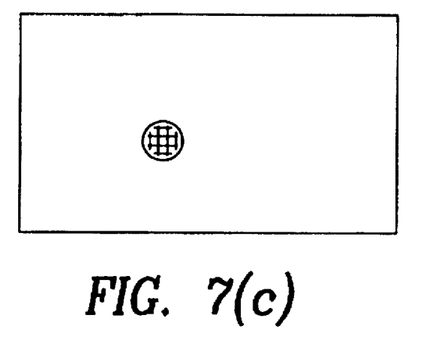
Figure 7D:
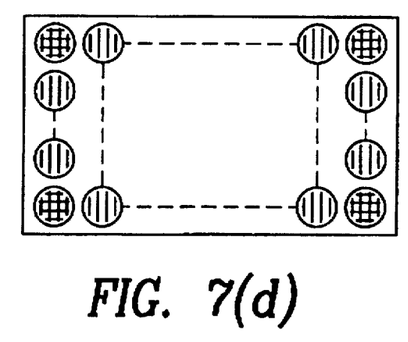
Figure 7E:
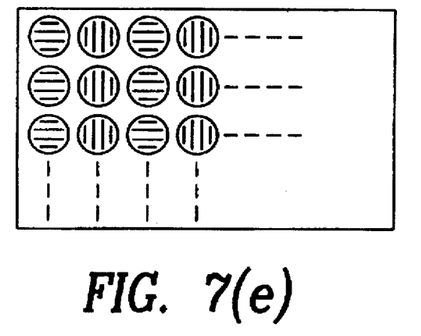
Figure 7F:
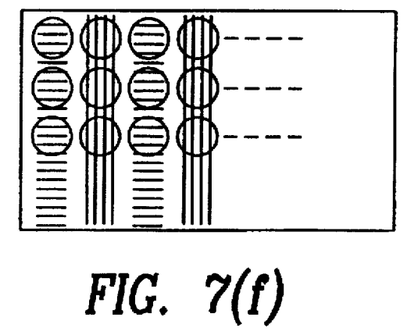
Figure 7G:
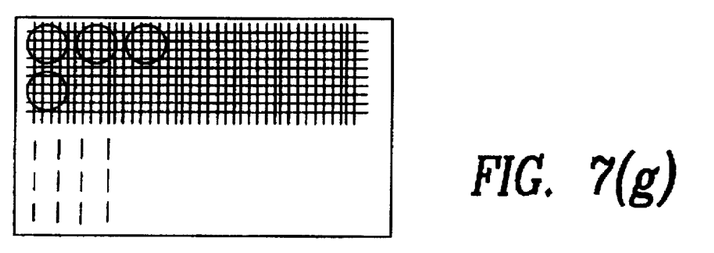

In FIGS. 7(a) to 7(e), the gratings beneath adjacent wells are discrete. In FIG. 7(a) the gratings beneath some of the wells extend at right angles to those beneath their neighbours. In FIG. 7(b) the gratings beneath the wells at the edges extend at right angles to those beneath the adjacent edge wells. In FIG. 7(c) the gratings beneath some of the wells extend in two, perpendicular directions. In FIG. 7(d), the gratings beneath wells at the edges in a row or column extend in two, perpendicular directions; the gratings beneath the remaining wells extending in one direction only. In FIG. 7(e), the gratings beneath all wells in a row or column extend at right angles to those beneath wells in adjacent rows or columns. In FIG. 7(f), the gratings beneath all wells in a row or column extend at right angles to those beneath wells in adjacent rows or columns but the gratings are continuous over the row or column. In FIG. 7(g), two perpendicular gratings extend continuously beneath all wells. Diffraction gratings orientated perpendicularly to each other permit the determination of the angle of autocollimation in the two normal directions and therefore the tilt of the base sheet 8.

The diffraction grating structure need not be positioned at the interface between the base sheet 8 and the waveguiding film 12 but can be positioned in the base sheet 8 or in the waveguiding film 12.

In another embodiment, a low index buffer layer may be positioned between the base sheet 8 and the waveguiding film 12 and the grating integrated in the base sheet 8. The grating may also be located at the surface opposite to the waveguiding film 12.

It will also be appreciated that the detection cell 2 may contain as many wells 6 as desired.

It will be appreciated that the invention can be used to detect the presence of antigens or antibodies in a sample and hence replace conventional immunoassays which require labelling of some sort. Also the invention can be used to detect antigens to receptors and vice versa. In further applications, the invention can be used to quantify nucleotide molecules in a sample and therefore the invention has application in PCR processes.

The invention provides the significant advantage that analysis of samples may be done in a highly automated, rapid fashion using, for the most part, conventional fluid handling equipment. Moreover, since optical biosensors do not require the use of radio-labels or large quantities of reagents, little, if any, hazardous waste is produced.

We claim:

1. A cell array plate comprising:

a microtitre sample plate having a matrix of bores extending from a first surface of said sample plate through said sample plate and to an opposite second surface of said sample plate, the bores being arranged in rows and columns;

a base plate arrangement having first and second opposite surfaces, and extending along said second opposite surface of said sample plate, said first surface of said base plate arrangement being in intimate contact with said opposite surface of said sample plate so as to seal said bores of said matrix along said opposite second surface of said sample plate, thereby closing said bores at a plurality of distinct surface areas; and a waveguiding film arrangement at said base plate arrangement and extending along said distinct surface areas, said base plate arrangement being transparent for light from said second surface of said base plate arrangement to said waveguiding film arrangement;

said base plate arrangement comprising at least one diffraction grating structure area adjacent each of said plurality of distinct surface areas for coupling light impinging through said second surface of said base plate arrangement into said waveguiding film arrangement along a distinct surface area, and from said waveguiding film arrangement adjacent said distinct surface area, back through said second surface of said base plate arrangement;

said base plate arrangement with said waveguiding film arrangement and said diffraction grating structure areas, substantially preventing light coupled into said waveguiding film arrangement at one of said plurality of distinct surface areas, from propagating into the waveguiding film arrangement at another one of said distinct surface areas neighboring said one of said distinct surface areas, and thereby substantially preventing cross-talk between said distinct surface areas.

2. The plate of claim 1, wherein said waveguiding film arrangement comprises at least two distinct diffraction grating structure areas at each of said distinct surface areas.

3. The plate of claim 1, wherein said waveguiding film arrangement comprises first diffraction gratings and second diffraction gratings, said first and second diffraction gratings being arranged in a rectangular pattern with respect to each other.

4. The plate of claim 1, including an optical coupling layer extending along each of said distinct surface areas.

5. The plate of claim 1, wherein said waveguiding film arrangement is made of titanium dioxide.

6. The plate of claim 1, wherein said waveguiding film arrangement is made of a material comprising at least one of the oxides $Ta_2O_5$, $HfO_2$, $Si_3N_4$, $ZrO_2$, niobium oxide, $Al_2O_3$ or a mixture of $SiO_2$ and $TiO_2$ or at least one of the oxinitrides HfON or SiON.

7. The plate of claim 1, wherein said base plate arrangement is removably connected to said sample plate.

8. The plate of claim 1, comprising at least three distinct diffraction gratings at each of said distinct surface areas.

9. The plate of claim 1, wherein said waveguiding film arrangement comprises a continuous waveguiding film.

10. The plate of claim 9, wherein a continuous diffraction grating structure area is provided along said base plate arrangement, forming said at least one diffraction grating structure area at each of said distinct surface areas.

11. The plate of claim 1, wherein said base plate arrangement includes a base plate, said waveguiding film arrangement being deposited on said base plate.

12. The plate of claim 11, wherein each diffraction grating structure area is provided at an interface between said waveguiding film arrangement and said base plate.

* * * * *